Figure 1:
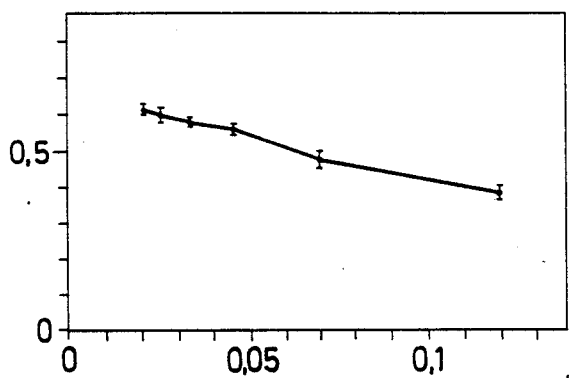

United States Patent [19]

Ranby

[11] Patent Number: 4,957,903

[45] Date of Patent: Sep. 18, 1990

[54] PHARMACEUTICAL AND CLINICAL COMPOSITIONS OF DESAA FIBRIN MONOMERS AND THE TETRAPEPTIDE GLY-PRO-ARG-PRO

[75] Inventor: Mats G. Rånby, Umeå, Sweden

[73] Assignee: Biopool International, Inc., New York, N.Y.

[21] Appl. No.: 936,347

[22] PCT Filed: Mar. 27, 1986

[86] PCT No.: PCT/SE86/00144

§ 371 Date: Nov. 20, 1986

§ 102(e) Date: Nov. 20, 1986

[87] PCT Pub. No.: WO86/05814

PCT Pub. Date: Oct. 9, 1986

[30] Foreign Application Priority Data

Apr. 1, 1985 [SE] Sweden .................. 8501614

[51] Int. Cl.$^5$ .............. C07K 5/10; C12Q 1/37; A61K 37/18

[52] U.S. Cl. .................. 514/18; 514/8; 514/21; 514/2; 530/330; 530/380; 530/381; 530/382; 530/383; 530/384; 530/806; 530/829; 435/13

[58] Field of Search ............. 514/2, 8, 21, 18; 530/382, 380, 381, 383, 384, 330; 424/101, 95

[56] References Cited

U.S. PATENT DOCUMENTS 3,966,701 6/1976 Dorman et al. .............. 530/382
4,455,290 6/1984 Olexa et al. .................. 530/382

OTHER PUBLICATIONS

Lewis et al., J. Biol. Chem., 260(18), 10192-9, (1985).
Hurlet-Jenson et al., Thrombosis Res., 27, 419-27, 1982.
Castellino et al., Ann., N.Y. Acad. Sci., 408, 595-601, (1983).
Furlan et al., Bioch. Biophys. Acta., 742, 25-32, (1983).
Laudano et al., P.N.A.S., 75(7), 3085-9, (1978).
Bale et al., P.N.A.S., 82, 1410-13, (Mar. 1985).
Weimer et al., Biol. Abs., 82(1): 1168, (1986 (Jul.)).
Belitser et al., Biokhymia, 50(8), 1336-41, (1985).
Ranby et al., Thromb. Res. 27, 743-9, (1982).
Laudano, Andrew P., and Doolittle, Russell F., *Biochemistry* 19, pp. 1013-1019 (1980).
Verheijen. J. H., Mullaart, E. et al., "A Simple, Sensitive Spectrophotometric Assay for Extrinsic (Tissue-Type) Plasminogen Activator Applicable to Measurements in Plasma", Thromb. Haemostas (Stuttgart) 48(3), 266-269 (1982).

(List continued on next page.)

*Primary Examiner*—Garnette Draper
*Assistant Examiner*—Jeff Kushan
*Attorney, Agent, or Firm*—Jones, Askew & Lunsford

[57] ABSTRACT

The invention relates to a fully solubilizable fibrin based composition, which is characterized by the combination that the fibrin is desAA-fibrin or desAA-fibrin from which the C-terminal portions of the α-chains have been removed by enzymatic digestion, and that the solubilizing agent is a tetrapeptide containing the amino acid sequence -L-prolyl-L-arginyl-, preferably glycyl-L-prolyl-L-arginyl-L-prolin.

The full solubility of the fibrin makes possible new uses within the area of determination of important fibrinolytical parameters, and the invention also relates to three such important alternative uses. A first use according to the invention is the use of the composition in connection with detection or quantification of the activity of the enzyme tissue plasminogen activator. A first alternative use means that the composition is usd for the detection of soluble fibrin in bioligical fluids, and a second alternative use means that the composition is used for measuring or studying fibrinolytic activity in vitro or in vivo through the addition of the composition and registration of the degradation of the fibrin.

43 Claims, 2 Drawing Sheets

OTHER PUBLICATIONS

Laudano et al., "Synthetic Peptides Modeled on Fibrin Polymerization Sites", Ann. N.Y. Acad. Sci. 408, pp. 315–329 (1983).

Chemical Abstracts vol. 98 (1983) Abstract No. 69 554, Biochyem. Biophys. Acta 1983, 742(1), 25–32.

Chemical Abstracts vol. 99 (1983), Abstract No. 118 035, Ann. N.Y., Acad. Sci. 1983, 408 (Mol. Biol. Fibrinogen Fibrin), 315–29.

Chemical Abstracts vol. 101 (1984), Abstract No. 106 025 Proc. Natl. Acad. Sci., U.S.A., 1984, 18 (14), 4339–42.

Chemical Abstracts vol. 88 (1983), Abstract No. 158 988a, Proc. Natl. Acad. Sci., U.S.A., 1978, 75(7), 3085–9.

Chemical Abstracts vol. 92 (1980), Abstract No. 125 912e, Biochemistry, 1980, 19(5), 1013–9.

Chemical Abstracts vol. 99 (1983) Abstract No. 118 035 Ann. N.Y., Acad. Sci., 1983, 408 (Mol. Biol. Fibrinogen Fibrin), 315–29.

PHARMACEUTICAL AND CLINICAL COMPOSITIONS OF DESAA FIBRIN MONOMERS AND THE TETRAPEPTIDE GLY-PRO-ARG-PRO

TECHNICAL FIELD

The present invention relates to a solubilizable, fibrin based composition which is based on a specific combination of a certain fibrin derivative and a low molecular peptide containing a certain amino acid sequence. The peptide referred to has, surprisingly, proved to give a complete solubilization of said specific fibrin derivative, which opens completely new possibilities of using such a composition when assaying important fibrinolytic parameters, or at least drastically improves the opportunity to perform accurate and reproducible analyses within this field. Hence, the invention also relates to certain especially interesting applications or uses of said composition.

BACKGROUND OF THE INVENTION

Systematic studies in fibrinolysis (those own systems of the body which are involved in the solubilization of fibrin, the protein from which blood clots are built up) has been hampered by difficulties in manipulating its target substance, fibrin. For further information on the fibrinolytic system see Collen D, 1980, Thrombosis and heamostasis 43: 77–86. The possibilities of replacing, for a model purpose, fibrin, which spontaneously forms a gel, with more easily handled substances, such as casein or albumin, are limited. This is due to the fact that fibrin, except from being the target substance, also has important regulatory functions in the fibrinolytic system. These can not be replaced by model proteins.

The demand for a soluble and hence easily handled fibrin derivative is substantial. Therefore, considerable research efforts have been made in order to satisfy this demand. In 1955, Donelly et al described in Arch. Biochem. Biophys. 56: 369–387, how fibrin can be solubilized in 1 mole/l of NaBr at pH 5.3. Further, in 1976, it was described by Haverkate and Timan in Progress in Chemical Fibrinolysis and Thrombolysis 2: 67–71, that fibrin can be solubilized with 10 mole/l of acetic acid, while in 1982 Ranby et al described in Thrombosis Research 27: 743–749, the solubilization of desAA-fibrin in 3.5 mole/l of urea.

However, neither of these methods has been widely used which confirms that they are not fully satisfactory. Thus, the described methods cause denaturation of the fibrin, which is expressed as a tendency of the fibrin to form, after having been brought back to physiological conditions, a precipitate instead of a gel. Furthermore, the described compositions of soluble fibrin do not stand being frozen/thawed or lyophilized/reconstituted with preserved properties.

As concerns prior art reference is also made to Chem. Abstracts 98 (1983), 69 554, which discloses a retardation of the polymerization of desAA-fibrin and desAABB-fibrin in the presence of Gly-Pro-Arg. However, the present invention is based on the fact that it has very unexpectedly turned out that there is a special type of tetrapeptide which does not only retard but also completely and permanently prevents the polymerization of a certain type of fibrin, viz. desAA-fibrin. This prevention has made it possible to prepare a practical useful preparation of soluble fibrin and even to find completely new areas of applications.

Furthermore, Chem. Abstracts 99 (1983), 118 035, discloses that "α-chain peptide" inhibits the polymerization of "thrombin-induced fibrin", i.e. desAABB-fibrin. Thus, said article is not relevant in connection with the present invention, according to which the above-mentioned tetrapeptide forms in combination with desAA-fibrin a stable, non-polymerizing composition.

Chem. Abstracts 101 (1984), 106 025, merely discloses that Gly-Pro-Arg-Pro retards the fibrin polymerization by being bound to fibrinopeptide A. Thus, this article is not either relevant in connection with the present invention; see above with reference to C.A. 99 (1983), 118 035.

SUMMARY OF THE INVENTION

According to the present invention it has unexpectedly turned out that the addition of a low molecular weight peptide containing the specific amino acid sequence -L-prolyl-L-arginyl- to a certain fibrin derivative, namely desAA-fibrin, gives a fully solubilizable composition, and at such a low concentration of the peptide that possibilities are opened for entirely new applications in connection with the determination of fibrinolytic components or that the accuracy and reproducibility of applications known per se are improved so that such applications can also come to a real practical use.

These results were not predictable for a person skilled in the art. It is true that in 1979 Laudano and Doolittle disclosed in Proceedings of the National Academy of Science 75: 3085–3089, that certain peptides, especially glycyl-L-prolyl-L-arginyl-L-prolin, have the ability to strongly reduce the polymerization rate for fibrin, but based upon this it was in no way possible to predict the extraordinary results which the present invention has been shown to give. Thus, it has e.g. turned out that desAA-fibrin is fully solubilized in a composition according to the invention at peptide concentration levels where the same peptide does not show any detectable solubilizing effect at all on desAABB-fibrin. In this context, it could be mentioned that desAA-fibrin differs from "normal" desAABB-fibrin by having only one pair of the fibriopeptides (the A-peptides) split off. DesAA-fibrin is commonly known as fibrin I, while desAABB-fibrin is named fibrin II, which denotations for simplicity will be used below.

Another important difference that has been demonstrated between fibrin I and fibrin II is that in the presence of the same peptide they differ essentially from each other as to the ability of stimulating the tissue activator in activation of plasminogen. Thus, a composition according to the invention containing fibrin I has been shown to be about 50% more effective than the corresponding composition containing fibrin II.

These and other properties will be further illustrated below in connection with the definition of the invention and in connection with the working examples.

More specifically the present invention relates to a solubilizable, fibrin based composition, which is characterized in that the fibrin is desAA-fibrin or desAAfibrin from which the C-terminal parts of the α-chains have been removed by enzymatic digestion, and that it comprises a solubilizing amount of a tetrapeptide containing the amino acid sequence -L-prolyl-L-arginyl-.

The preferred tetrapeptide for use in the composition claimed is glycyl-L-protyl-L-arginyl-L-prolin, but the invention is not limited thereto, as there should exist other tetrapeptides containing the specified amino acid sequence which give essentially the same effect. The desAA-fibrin used in the compositions according to the invention is preferably prepared by a selective removal of merely fibrinopeptide A from fibrinogen by enzymes, e.g. batroxobin extracted out of venom from snakes of the Bothrops genus.

The solubilizing concentration of the tetrapeptide can of course be determined from case to case using routine tests. Generally, however, the lowest concentration for practical use of the composition should be about 0.4 mg per ml of a ready to use-composition or ready to use-preparation. The upper limit is more difficult to generalize and is influenced by different factors, such as economic considerations and intended use of the composition. Thus, the economy may be decisive for a suitable upper limit, as for financial reasons one will of course not use higher concentrations than are required for the intended purpose. However, in the use as a stimulator in determining the tissue activator there is an upper limit for the useful end concentration of the peptide.

This is about 10 mg/ml and is justified by the fact that the activation reaction is inhibited at peptide concentrations exceeding about 0.03 mg/ml and by the fact that at least one threehundredths volume of fibrin preparation has to be added at the beginning of the reaction $(0.033 \times 300 = 10)$. Generally a suitable range is 0.4–10 mg/ml of ready to use-preparation, an especially interesting range being 0.6–4 mg/ml. In many cases optimum results can be achieved at a concentration of about 2 mg/ml.

The composition according to the invention comprising fibrin I solubilized with the indicated peptide is preferably presented in a physiological buffer, which for instance means that it can be administered without any inconvenience into the circulatory tract, e.g. injected intraveneously.

The preparation of the composition according to the invention is not associated with any particular problems but can preferably be made by first digesting the fibrinogen with enzyme and then dissolving the resulting fibrinogel by the addition of peptide. If required, the enzyme can then be removed, e.g. with matrix-bound antibodies against the same.

As was mentioned above, the invention also refers to certain particular applications or uses of the composition, which have been made possible or have been substantially improved as compared to the prior art by the suprior properties of the soluble fibrin preparation that is the result of the invention. These uses can be assigned to the determination of important fibrinolytic parameters, the background being as follows.

Fibrin deposits in the circulatory tract are degraded to soluble components by the serine protease plasmin. This enzyme is formed from the plasma protein plasminogen by action of plasminogen activators. The known plasminogen activators are serine proteases, which split an Arg-Val-peptide bond in the plasminogen molecule to form the active two chain enzyme plasmin.

Plasmin shows some substrate specificity and preferably splits peptide bonds in the fibrin matrix and in the fibrin precursor fibrinogen. This specificity is far from absolute, and plasmin sensitive bonds can be found in most proteins (many of the numerous trypsin sensitive bonds are also split by plasmin). Plasmin formed during fibrinolysis may therefore damage plasma proteins and cell surface proteins. In order to avoid this organism has developed mechanisms that localize the plasmin formation and restrict its effect. Two such mechanisms are commonly recognized, namely:

1. The tissue plasminogen activator (t-PA), an important plasminogen activator in the blood, is effective only in the presence of fibrin. In the absence of fibrin the rate of the t-PA-catalyzed plasminogen activation is low, but in the presence of fibrin the reaction rate is increased up to 1000 times. The generation of plasmin is, thus, localized to fibrin, which is then degraded. When the fibrin is once degraded, the rate of plasmin formation returns to low values.

2. Generated plasmin not involved in fibrin degradation is rapidly inhibited by the plasmin inhibitor $\alpha$-2-antiplasmin. The effect of generated plasmin is, thus, limited to the vicinity of the clot.

Normally, fibrin clots have a useful function, and consequently they should not be exposed to premature lysis. By this reason nature has developed mechanism to avoid this, and these mechanisms are at present beginning to be better understood. The now discovered fast acting plasminogen activator inhibitor can constitute the base for such a mechanism. Alterations, during fibrinolysis, of the stimulatory properties of the fibrin can constitute another one.

The present invention relates to certain uses, which are related to the above-mentioned. One first use of the composition more specifically implies that it is used in connection with the detection or determination or quantification of the enzyme tissue plasminogen activator (t-PA), the fibrin potentiating the activity of the enzyme towards the physiological substrate plasminogen or towards some synthetic substrate.

The method per se, i.e. analysis with respect to tissue plasminogen activator, is previously disclosed by Rånby et al in Thrombosis Research (1982) 27: 743–749. However, according to the invention it has been shown that the fibrin composition according to the invention is considerably more effective than the composition described in said publication as regards the ability of stimulating the tissue plasminogen activator in the activation of plasminogen. Furthermore, when diluting fibrin I solubilized with the peptide referred to, fibrin gel is formed more slowly than when diluting fibrin I solubilized with urea. This is of a substantial practical significance when solubilized fibrin I is used as a "stimulator" in the determination of t-PA according to the above-mentioned method. The effects of the composition claimed will be further elucidated below.

An alternative application or use according to the invention of the composition means that it is utilized to detect trace amounts of fibrin dissolved in biological fluids, e.g. blood plasma, the composition being used as a standard. This use is made possible inter alia by the favourable gel forming kinetic shown by the fibrin composition according to the invention, and the composition according to the invention will most likely be of a great practical importance. Thus, the concentration of fibrin in blood or in blood plasma is expected to become an important diagnostic parameter inter alia for the condition D.I.C. (disseminatded intravascular coagulation).

A second alternative application or use according to the invention is the use of the composition in measuring or studying fibrinolytic activity in vitro or in vivo through the addition of the composition and registration or recordal of the degradation of the fibrin contained in the composition. In connection with this use, the unique fact should be emphasized that the fibrin composition according to the invention is most likely non-toxic and is presented in a physiological buffer, so that the composition can be administered without any inconvenience into the circulatory tract, e.g. by intravenous injection. The fibrin will, inter alia owing to its gel formation kinetics, be distributed over the entire circulatory tract, where it is most likely complexed to fibrinogen. Due to fibrinolytical activity in the blood and in the vascular bed this fibrin will be degraded and disappear out of circulation. The rate at which this occurs is a measure of the total fibrinolytical capacity of the organism. This parameter, which can also be measured in vitro, may come to be of a great diagnostic importance, whereby the composition according to the invention will be an extremely valuable instrument in such a diagnosis. The composition according to the invention is for instance an extraordinarily well suited fibrin derivative for use in vivo, as it is presented in a physiological buffer and as the peptide is likely to be harmless to the organism. To facilitate the analysis the fibrin can be labelled, e.g. with radio labelled iodine or with biotin.

EXAMPLES

The invention will now be illustrated further by some working examples, which are presented merely to illustrate the invention and not in any restricting sence.

In the examples highly purified preparations of proteins and some less known chemicals are used. These are described below together with information on where they can be obtained. The compositions of buffers used are also indicated.

Glu-Plasminogen from human plasma; lyophilized preparation from BioPool AB, Umeå, which according to specifications contains less than 1% of Lys-plasminogen, less than 10 ppm of plasmin and less than 0.0001 IU of t-PA/mg. At use the preparation was reconstituted in sterile PBS (see below), to a final concentration of 5 mg/ml and centrifuged 2 min at 11.000× g. Reconstituted material was kept at +4° C. for no more than 48 hours.

Tissue plasminogen activator, (t-PA), in its single-chain form from human melanoma cells; lyophilized preparation without any carrier substance from BioPool AB, Umeå, According to the manufacturer; specific activity 500,000 IU/mg, more than 95% active, containing less than 2% of two chain t-PA and less than 1% of non t-PA protein. The preparation was reconstituted in 1M KHCO$_3$ to a concentration of 50,000 IU/ml and kept at +4° C. for no more than 48 hours. Further dilution was made with Tris/Tween buffer, (see below). As a reference for t-PA activity the WHO first international standard lot 83/517 from NIBSAC, Holly Hill, London, was used.

Fibrinogen from human plasma; lyophilized preparation from Imco Corporation Ltd AB, Stockholm, according to specifications 97% coagulability and free from plasminogen. The preparation was reconstituted with H$_2$O to a concentration of 20 mg/ml and was kept a +4° C. for at most 4 hours.

Batroxobin from snake venom from Bothrops atrox maranhao; lyophilized preparation from Pentapharm AG, Basel, Switzerland. According to specifications at leasts 100 BU/ml. The preparation was reconstituted in PBS to a concentration of 20 BU/ml and kept as 0.2 ml aliquotes in liquid nitrogen (−196° C.).

Thrombin from bovine plasma; sterile solution Topostasin from Hoffman-La Roche, Basel, Switzerland.

Gly-Pro-Arg-Pro, (glycyl-L-prolyl-L-arginyl-L-prolin), as the acetate salt from BioPool AB, Umeå. The salt was dissolved in H$_2$O to a concentration of 100 mg/ml and kept at −20° C.

Plasmin substrate Spectrozyme PL. (H-D-norleucyl-L-hexahydrotyrosyl-L-lysinyl-paranitro-anilide); lyophilized preparation from American Diagnostica Inc., Greenwich, USA.

Buffers: PBS ("phosphate buffered saline"), with the composition 0.1 mole/l of NaCl, 0.02 mole/l of sodium phosphate buffer pH 7.3.

Tris/Tween has the composition 0.1 mol/l of Tris/acetic acid buffer pH 8.3 (at 37° C.), containing 0.1 g/l of Tween 80.

EXAMPLE 1

Fibrinogen, 5 mg/ml, dissolved in PBS was aliquoted as 2 ml aliquotes in φ9 mm polystyrene test tubes. To these either 0.01 ml of bovine thrombin, 20 NIH/ml, or 0.01 ml of batroxobin (from B A Maranhao), 20 BU/ml was added. Hereby, in all test tubes, a coagulate was formed within 5 minutes.

To these small fibrin coagulates 0.02 ml of glycyl-L-prolyl-L-arginyl-prolin, (Gly-Pro-Arg-Pro), with a protein concentration between 0 and 115 mg/ml, was added. The final concentration of peptide in the coagulates was, thus, between 0 and 10 mg/ml.

Every twenty minute the test tubes were shaken, and after 3 hours the appearance of the coagulates were registered. The experiment was performed at room temperature (about 20° C.). The results are presented in Table 1 below.

TABLE 1

| Solubility for fibrin I and fibrin II, respectively | | | | | | | | | |
|---|---|---|---|---|---|---|---|---|---|
| Conc. mg/ml | 0 | 0.1 | 0.2 | 0.4 | 0.6 | 1.0 | 2.0 | 4.0 | 10.0 |
| fibrin I (obtained with batroxobin) | rigid gel | soft gel | soft gel | weakly opaque sol. | clear sol. | clear sol. | clear sol. | clear sol. | clear sol. |
| fibrin II (obtained with thrombin) | rigid gel | rigid gel | rigid gel | rigid gel | rigid gel | rigid gel | rigid opaque gel | rigid opaque gel | loose gel |

From Table 1 above it can be seen that solubilization of fibrin I was achieved already at a concentration of about 0.4 mg/ml and that full solubilization of the fibrin referred to was achieved at a peptide concentration of 0.6 mg/ml or more. On the contrary no solubilization of fibrin II could be obtained within the concentration range tested. As 10 mg/ml may be a practicable upper limit for certain applications, as suggested above, and as will be further illustrated below, it is clear that merely the combination of peptide with fibrin I is practically useful.

EXAMPLE 2

Preparation of peptide solubilized fibrin I (used in Examples 3, 4 and 5). 1 volume 20 mg/ml of fibrinogen was diluted with 1 volume of PBS. To this one eightieth volume 20 BU/ml of batroxobin (end concentration 0.25 BU/ml) was added, and incubation was performed at room temperature (18° C.). A soft gel was formed within 15 minutes. After 90 minutes the gel was solubilized by the addition of one fifthieth volume of 100 mg/ml of Gly-Pro-Arg-Pro (final concentration in the coagulate 2 mg/ml). Gentle agitation for 3 hours.

The solution was sterile filtered (0.45 μm membrane filter), and aliquoted as 100 μl aliquotes (1 mg of fibrin I, 0.2 mg of peptide). Some of these were kept at −20° C., (lot 12A), and some were lyophilized and kept under a nitrogen atmosphere at +4° C. (lot 12B).

The t-PA stimulating property of these preparations were tested and compared with an earlier lyophilized preparation (lot 11B, see Table 2). The lyophilized preparations, (lot 11B and lot 12B), were reconstituted by the addition of 100 μl of Tris/Tween. Lot 12B2d is a reconstituted material kept at +4° C. for 2 days.

Table 2. 0.5 ml aliquotes of 0.5 mg/ml of Glu-plasminogen, 0.5 mM Spectrozyme and 0.2 IU/ml of one chain t-PA dissolved in Tris/Tween were dispensated in 9 mm polystyrene tubes. To these tubes 1, 3, 5 or 7 μl of solubilized fibrin I derivative were added, and immediately after the additions the tubes were agitated and placed in a water bath held at 37° C. After 1 h of incubation the reaction was stopped by addition of 50 μl of 10% acetic acid and the absorbance at 405 nm was measured. The increase in absorbance was calculated by subtracting the absorbance in solution where the reaction was stopped immediately after addition of fibrin. This absorbance was 0.083. In the absence of stimulator an incubation at 37° C. for 4 hours resulted in an absorbance increase of 0.017.

TABLE 2

| Added amount of fibrin I prep (μl) | Absorbance increase at 405 nm obtained with different preparations of solubilized fibrin I | | | |
|---|---|---|---|---|
| | lot 11B | lot 12A | lot 12B | lot 12B2d |
| 1 | 0.635 | 0.621 | 0.572 | 0.562 |
| 3 | 0.755 | 0.714 | 0.705 | 0.688 |
| 5 | 0.800 | 0.787 | 0.776 | 0.750 |
| 7 | 0.809 | 0.804 | 0.795 | 0.778 |

The results in Table 2 show that soluble fibrin compositions, prepared according to the invention, can be prepared with reproducible t-PA stimulatory effects. Furthermore it is demonstrated that this stimulatory effect is on the whole unaffected by lyophilization with subsequent reconstitution.

Finally, it is shown that reconstituted preparations have practically acceptable stabilities (48 h). Taken together the experiment shows that soluble fibrin, prepared according to the invention, has properties that make it extremely well suited for the determination of t-PA activity.

EXAMPLE 3

In order to determine to what extent the peptide Gly-Pro-Arg-Pro inhibits the fibrin stimulated t-PA activation of plasminogen the following experiment was performed. To aliquotes of 0.49 ml of Tris/Tween, containing 0.025 mg of Glu-plasminogen, 0.25 μmole of Spectrozyme and 0.1 IU of t-PA, there was added 0.01 ml of peptide, at a concentration of 5, 2.5, 1.25, 0.63, 0.32 or 0 mg/ml.

The reaction was started by addition of 5 μl of soluble fibrin according to the invention (see Example 2) and as the fibrin preparation contains 2 mg/ml of the peptide the final peptide concentrations were 0.12, 0.07, 0.045, 0.0325, 0.0263, and 0.2 mg/ml. 60 minutes at 37° C. after the fibrin addition the reaction was stopped by the addition of 50 μl of 10% acetic acid and the absorbance at 405 nm was measured. At each peptide concentration 4 experiments were performed and the mean values of the absorbance increase and its standard deviations are accounted for in FIG. 1. Thus, FIG. 1 shows the t-PA stimulating effect of 0.1 mg/ml of soluble fibrin according to the invention, dependent on the final concentration of peptide. More specifically the ordinate denotes the absorbance increase at 405 nm, while the abscissa denotes the final concentration of Gly-Pro-Arg-Pro in mg/ml. In the absence of fibrin the absorbance increase was about 0.006 at all examined peptide concentrations.

From the experiment it is clear that a final concentration of 0.033 mg/ml of peptide results in a significant decrease in t-PA mediated activation of Glu-plasminogen. In this way an upper limit for a useful final concentration of peptide in the preparation of soluble fibrin according to the invention is provided. This is 10 mg/ml and is motivated by the activation reaction being inhibited at peptide concentrations exceeding 0.033 mg/ml and by the fact that at least one threehundredth volume of fibrin preparation has to be added at the beginning of the reaction ($0.033 \times 300 = 10$).

EXAMPLE 4

The determination of t-PA activity while utilizing soluble fibrin according to the invention can be made in the following way: 500 μl of TAR (tissue plasminogen activator reagent) consisting of 0.05 mg/ml of Glu-plasminogen and 0.5 mM of Spectrozyme PL dissolved in Tris/Tween are aliquoted in ϕ9 mm polystyrene test tubes. To these 50 μl samples consisting of the WHO t-PA standard diluted in Tris/Tween (t-PA concentrations between 0 and 3 IU/ml) are added. To this (immediate mixing) 5 μl soluble fibrin I is added, as is described in Example 2. After 60 minutes at 37° C. the reaction is stopped by 50 μl of 10% acetic acid. The absorbance increase at 405 nm is determined as in Example 2 and is plotted along the ordinata against the t-PA content in the sample (IU/ml), FIG. 2.

Figure 2:
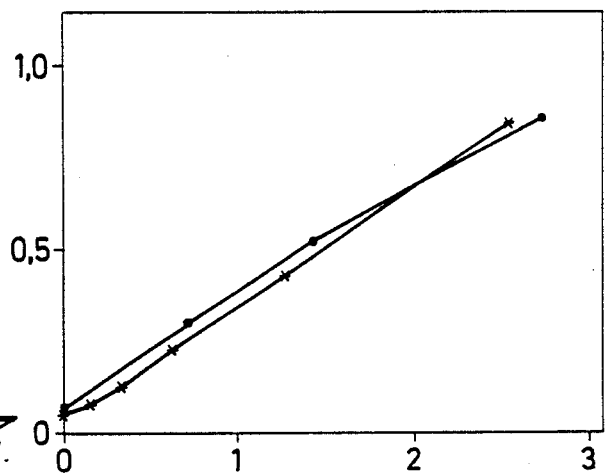

To demonstrate the determination of t-PA in plasma samples 10 μl of t-PA dissolved in Tris/Tween were added to 200 μl of t-PA depleted plasma to yield final concentrations between 0 and 20 IU/ml. To destroy the plasmin inhibitor content of the plasma 200 μl of 1M acetate buffer pH 3.9 were added, followed by a 15 minutes incubation at 37° C. After that 200 μl of Tris/Tween were added, whereby the t-PA concentration became 0–2.5 IU/ml. 50 μl samples thereof were analyzed for t-PA activity as described above. The result is shown in FIG. 2. The figure shows the analysis of t-PA dissolved in buffer (•) and of t-PA dissolved in blood plasma (*).

From FIG. 2 it can be seen that soluble fibrin according to the invention is extraordinarily useful in the determination of t-PA activity with application to biological samples. The content of inhibitors for t-PA is determined by adding a known amount of t-PA to the sample, whereafter the residual excess of t-PA is determined. Fibrin preparations according to the invention are, thus, very useful also for the determination of the content of t-PA inhibitor in e.g. blood or blood plasma.

In the t-PA measurements in Examples 2 and 3 a solution containing 0.05 mg/ml of plasminogen was used. During the measurement less than 1% thereof is activated. Thus the high concentration of plasminogen is not justified by the consumption but by the fact that a high activation rate, meaning sensitivity, demands such concentrations.

However, during the development of the invention it was found that partially degraded fibrin (fibrin with C-terminal parts of the α-chains split off) can stimulate t-PA to effectively activate plasminogen at plasminogen concentrations of 0.005 mg/ml. Soluble fibrin according to the invention, where the C-terminal parts of the α-chains have been removed from the fibrin by enzymatic digestion, e.g. with matrix bound plasmin, would allow t-PA measurement with considerably lower plasminogen consumption. Plasminogen of the necessary high quality is an expensive component in tPa measurements, which means that the possibility of reducing the concentration is of great importance.

EXAMPLE 5

Fibrin may be found in circulating blood, where it most likely occurs in the form of complexes with other plasma proteins. The presence of such fibrin indicates proceeding coagulation processes and a quantification of circulating fibrin is likely to be of a great clinical interest.

The ability of the tissue plasminogen activator of activating plasminogen is greatly potentiated by fibrin as was described above. If the concentration of fibrin is low, the activation rate depends directly thereupon, as was shown by Ranby M, 1982, Biochimica and Biophysica Acta 704: 461–469. In connection with work on the present invention it was noted that also fibrin in plasma stimulated the capacity of t-PA to activate plasminogen and that this could constitute a principle on which analytical methods for the determination of fibrin could be based. However, for such methods there will arise a need for a standard and soluble fibrin according to the invention is here demonstrated to be a good, perhaps the only practicable one, standard for this purpose.

Figure 3:
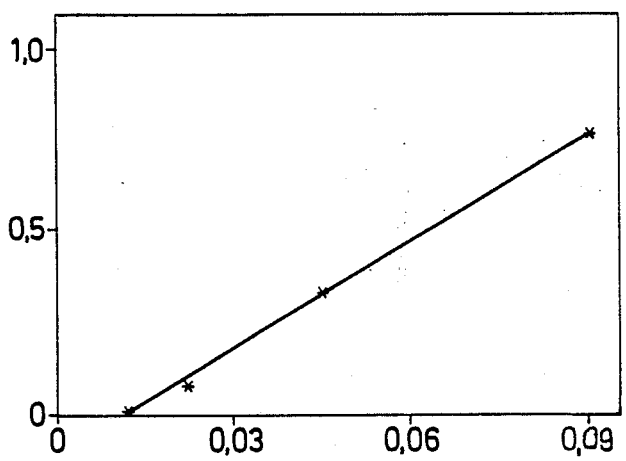

To 1 ml of human blood plasma 10 $\mu$l of soluble fibrin according to the invention were added (see Example 2). This plasma (containing 0.09 mg/ml of added fibrin) was diluted with plasma, plasma samples containing 0.09, 0.045, 0.023, 0.011, and 0.0056 mg/ml being made. From these samples 50 $\mu$l were mixed with 500 $\mu$l of 0.05 mg/ml of plasminogen, 0.5 mM Spectrozyme and 50 IU/ml of t-PA. After 25 minutes at 37° C. the reactions were stopped by the addition of 50 $\mu$l of 10% acetic acid. The absorbance increase at 405 nm was determined and plotted along the ordinata as a function of the concentration of added fibrin, FIG. 3.

The results here accounted for demonstrate that soluble fibrin according to the invention is well suited as a standard in analyses aiming at the determination of the fibrin content in circulating blood or blood plasma.

EXAMPLE 6

It seems probable that an important function of the fibrinolysis system is to free circulating blood from low amounts of fibrin (see Example 5). Probably the enzyme tissue plasminogen activator (t-PA) is of significance in this respect, but also other enzymes may be involved. Reasonably, what is of importance in clinical connections is not which enzyme or enzymes is (are) active, but the results of their action. Therefore, the soluble fibrin according to the invention may become of a great diagnostic importance as this makes it possible to add to blood, in vivo or in vitro, or to blood plasma a controlled amount of fibrin. The efficiency of the fibrinolytic system can then be established by recording how this added fibrin is degraded. The key to this type of determination is a handleable fibrin derivative.

In the present example there is added to normal blood plasma a certain amount of soluble fibrin (70 mg/l or 200 nmole/l). At regular intervals samples are taken and the concentration of remaining fibrin is determined by the method disclosed in Example 5. The experiment is also performed after an increase of the t-PA activity in plasma of 10 IU/ml.

To two 600 $\mu$l samples of normal blood plasma there were added 10 $\mu$l of Tris/Tween (sample A) or 10 $\mu$l of 600 IU/ml of one-chain t-PA (sample B). To these two samples there were added 4 $\mu$l of peptide solubilized fibrin I (see Example 2), the plasma samples containing 70 mg/l of added fibrin. Immediately after the addition of fibrin (time=0) and at 5, 10, 20 and 30 minutes aliquotes were taken from the plasma samples and the fibrin concentrations were determined as in Example 2.

Figure 4:
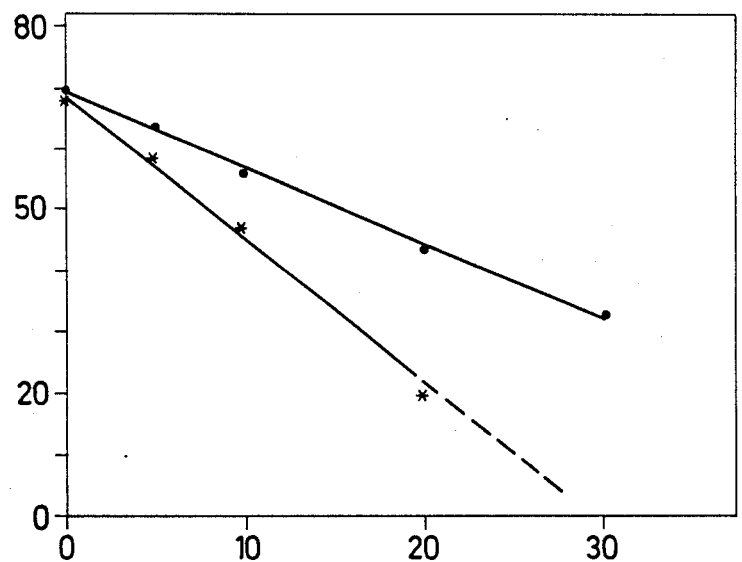

The results are presented in FIG. 4, where the ordinata shows the remaining fibrin concentration in mg/l and the abscissa shows the incubation time in minutes. Thus, soluble fibrin according to the invention was added to normal human plasma (•) and to normal human plasma enriched with 10 IU/ml of t-PA (x). After the additions the concentration of fibrin was in each case 70 mg/l. The plasma samples were incubated at 25° C. and aliquotes were analyzed for fibrin at 0, 5, 10, 20 and 30 minutes.

From the results (see FIG. 4) it is clear that the fibrin concentration of sample A fell from 70 mg/l at the time 0 to 48 mg/l after 20 minutes. The corresponding figures for sample B were 70 mg/ml (time 0) and 20 mg/ml (20 minutes). Thus, soluble fibrin disappears rather rapidly when added to normal plasma. This process will be even more rapid if the fibriolytic activity in plasma is increased by the addition of t-PA. The ability of blood to make itself free from circulating soluble fibrin can be expected to be reduced for patients with a tendency to thrombosis and/or infarct. The soluble fibrin according to the invention makes possible a quantification of said ability.

I claim:

1. A solubilizable, fibrin based composition, consisting of:
    (a) approximately 0.1 to 20 mg/ml desAA-fibrin, and
    (b) approximately 0.4 to 10 mg/ml of a peptide consisting of glycyl-L-prolyl-L-arginyl-L-proline,
    wherein the peptide prevents polymerization of said desAA-fibrin, thus solubilizing said desAA-fibrin to form a stable, non-polymerizing composition.

2. The composition of claim 1, wherein the desAA-fibrin has been obtained by a selective removal of fibrinopeptide A from fibrinogen with an enzyme.

3. The composition of claim 1, wherein the peptide concentration is 0.6–4 mg/ml.

4. The composition of claim 1 which additionally includes a physiological buffer.

5. The composition of claim 2, wherein said enzyme is batroxobin.

6. The composition of claim 1, wherein the peptide concentration is about 2 mg/ml.

7. A method for the detection or quantification of tissue plasminogen activator in a sample comprising the steps of:
   (a) incubating the sample, plasminogen, a plasmin substrate and a soluble fibrin composition consisting of approximately 0.1 to 20 mg/ml desAA-fibrin and approximately 0.4 to 10 mg/ml of a peptide consisting of glycyl-L-prolyl-L-arginyl-L-proline, so that any tissue plasminogen activator in the sample causes the formation of plasmin which causes cleavage of the plasmin substrate; and
   (b) measuring the amount of plasmin substrate cleaved.

8. A method for the detection or quantification of plasminogen in a sample comprising the steps of:
   (a) incubating the sample, a tissue plasminogen substrate and a soluble fibrin composition consisting of approximately 0.1 to 20 mg/ml desAA-fibrin and approximately 0.4 to 10 mg/ml of a peptide consisting of glycl-L-prolyl-L-arginyl-L-proline, so that any tissue plasminogen activator in the sample causes cleavage of the tissue plasminogen substrate; and
   (b) measuring the amount of substrate cleaved.

9. The method of claim 8, wherein the plasmin substrate is a paranitro anilide.

10. The method of claim 9, wherein the paranitro anilide is H-D-norleucyl-L-hexahydrotyrosyl-L-lysinyl-paranitro-anilide.

11. The method of claim 8, wherein the product is cleaved plasmin substrate.

12. A method for the detection or quantification of tissue plasminogen activator in a sample comprising the steps of:
   (a) incubating the sample with a synthetic tissue plasminogen activator substrate, and a soluble fibrin composition consisting of approximately 0.1 to 20 mg/ml desAA-fibrin and approximately 0.4 to 10 mg/ml of a peptide consisting of glycyl-L-prolyl-L-arginyl-L-proline, so that any tissue plasminogen activator in the sample causes cleavage of the tissue plasminogen substrate; and
   (b) measuring the amount of substrate cleaved.

13. The method of claim 12, wherein the product is cleaved tissue plasminogen activator substrate.

14. A solubilizable, fibrin based composition, consisting of:
   (a) approximately 0.1 to 20 mg/ml desAA-fibrin from which the C-terminal portions of the α-chains have been removed from some of the desAA-fibrin by enzymatic digestion with plasmin, and
   (b) approximately 0.4 to 10 mg/ml of a peptide consisting of glycyl-L-prolyl-L-arginyl-L-proline, wherein, the peptide prevents polymerization of said desAA-fibrin, thus solubilizing said desAA-fibrin to form a stable, non-polymerizing composition.

15. The composition of claim 14, wherein the desAA-fibrin has been obtained by a selective removal of fibrinopeptide A from fibrinogen with an enzyme.

16. The composition of claim 15, wherein the enzyme is batroxobin.

17. The composition of claim 14, wherein the peptide concentration is 0.6–4 mg/ml.

18. The composition of claim 17, wherein the peptide concentration is approximately 2 mg/ml.

19. The composition of claim 14, which additionally includes a physiological buffer.

20. A method for the detection or quantification of tissue plasminogen activator in a sample comprising the steps of:
   (a) incubating the sample with plasminogen, a plasmin substrate, and a stable, soluble composition consisting of approximately 0.1 to 20 mg/ml desAA-fibrin from which the C-terminal portions of the α chain have been removed from some of the desAA-fibrin by enzymatic digestion with plasmin, and approximately 0.4 to 10 mg/ml of a peptide consisting of glycyl-L-prolyl-L-arginyl-L-proline so that any tissue plasminogen activator in the sample causes cleavage of the plasmin substrate; and
   (b) measuring the amount of plasmin substrate cleaved.

21. The method of claim 20, wherein the product is cleaved plasmin substrate.

22. The composition of claim 14, wherein the plasmin comprises matrix bound plasmin.

23. The method of claim 20, wherein the desAA-fibrin has been obtained by a selective removal of fibrinopeptide A from fibrinogen with an enzyme.

24. The method of claim 23, wherein the enzyme is batroxobin.

25. The method of claim 20, wherein the peptide concentration is 0.6 to 4 mg/ml.

26. The method of claim 20, wherein the peptide concentration is 2 mg/ml.

27. The method of claim 20, wherein the soluble composition additionally includes a physiological buffer.

28. The method of claim 20, wherein the plasmin comprises matrix bound plasmin.

29. The method of claim 7, wherein the desAA-fibrin has been obtained by a selective removal of fibrinopeptide A from fibrinogen with an enzyme.

30. The method of claim 29, wherein the enzyme is batroxobin.

31. The method of claim 7, wherein the peptide concentration is 0.6 to 4 mg/ml.

32. The method of claim 7, wherein the peptide concentration is 2 mg/ml.

33. The method of claim 7, wherein the soluble fibrin composition additionally includes a physiological buffer.

34. The method of claim 8, wherein the desAA-fibrin has been obtained by a selective removal of fibrinopeptide A from fibrinogen with an enzyme.

35. The method of claim 34, wherein the enzyme is batroxobin.

36. The method of claim 8, wherein the peptide concentration is 0.6 to 4 mg/ml.

37. The method of claim 8, wherein the peptide concentration is 2 mg/ml.

38. The method of claim 8, wherein the soluble fibrin composition additionally includes a physiological buffer.

39. The method of claim 12, wherein the desAA-fibrin has been obtained by a selective removal of fibrinopeptide A from fibrinogen with an enzyme.

40. The method of claim 39, wherein the enzyme is batroxobin.

41. The method of claim 12, wherein the peptide concentration is 0.6 to 4 mg/ml.

42. The method of claim 12, wherein the peptide concentration is 2 mg/ml.

43. The method of claim 12, wherein the soluble fibrin composition additionally includes a physiological buffer.

* * * * *